United States Patent
Ballew et al.

(10) Patent No.: US 10,843,186 B1
(45) Date of Patent: Nov. 24, 2020

(54) CLOSED FLUID RECEIVING AND SAMPLING CONTAINER

(71) Applicant: SANI-TECH WEST, INC., Camarillo, CA (US)

(72) Inventors: Chris Ballew, Thousand Oaks, CA (US); Richard Shor, Moorpark, CA (US)

(73) Assignee: SANI-TECH WEST, INC., Camarillo, CA (US)

( * ) Notice: Subject to any disclaimer, the term of this patent is extended or adjusted under 35 U.S.C. 154(b) by 0 days.

(21) Appl. No.: 16/903,270

(22) Filed: Jun. 16, 2020

(51) Int. Cl.
  *B01L 3/00* (2006.01)
  *B01L 9/06* (2006.01)
  *B01L 3/02* (2006.01)

(52) U.S. Cl.
  CPC ............ *B01L 3/502* (2013.01); *B01L 3/0217* (2013.01); *B01L 9/06* (2013.01); *B01L 2200/12* (2013.01); *B01L 2300/042* (2013.01); *B01L 2300/048* (2013.01); *B01L 2300/06* (2013.01); *B01L 2300/12* (2013.01); *B01L 2300/123* (2013.01); *B01L 2400/06* (2013.01)

(58) Field of Classification Search
  CPC ..................................................... B01L 3/502
  See application file for complete search history.

(56) References Cited

U.S. PATENT DOCUMENTS

| | | | | |
|---|---|---|---|---|
| 6,136,274 A | * | 10/2000 | Nova | B01J 19/0046 422/509 |
| 2007/0034592 A1 | * | 2/2007 | Pavlovic | B01L 3/50825 215/253 |
| 2009/0042280 A1 | * | 2/2009 | Yang | B01L 3/5027 435/287.2 |
| 2013/0330250 A1 | * | 12/2013 | Koeda | C12N 15/1013 422/527 |
| 2016/0018295 A1 | * | 1/2016 | Whitcomb | F16K 5/0214 73/864.64 |
| 2016/0108356 A1 | * | 4/2016 | Shor | C12M 27/02 435/297.1 |

OTHER PUBLICATIONS

SaniSure, Engineered Single Use Solutions . . . Reducing Operational Cost, Improving Production Efficiency, Brochure, published in 2009, http://www.sani-techwest.com/Literature/Cap2v8.pdf, last accessed Jun. 16, 2020, 2 total pages.

(Continued)

*Primary Examiner* — Matthew D Krcha
(74) *Attorney, Agent, or Firm* — SoCal IP Law Group LLP; Guy Cumberbatch; Steven Sereboff

(57) ABSTRACT

A closed fluid receiving and sampling container that enables transfer of valuable reaction liquid to a receptacle without risking loss of sterility. The sampling container has a dip tube subassembly with a shorter inlet tube bent towards the wall of the receptacle to prevent or reduce foaming, and a longer outlet tube used to drain the waste liquid once the magnetic beads are trapped by the magnet. The dip tube subassembly is injection molded in one piece and provides a sealed lid also with a vent tube therethrough to enable filling and draining the receptacle without removing the lid, thus keeping the process aseptic. The sampling container is especially useful in the context of magnetic bead separation processes.

27 Claims, 4 Drawing Sheets

(56) References Cited

OTHER PUBLICATIONS

Thermo Fisher Scientific, Dynabeads magnetic beads, brochure, published in 2019, http://assets.thermofisher.com/ TFS-Assets/BID/brochures/dynabeads-magnetic-beads-brochure.pdf, last accessed Jun. 16, 2020, 24 total pages.
Thermo Fisher Scientific, Magnets for Molecular and Cell Separation Applications, product purchase page, https://www.thermofisher.com/us/en/home/brands/product-brand/dynal/magnets.html, last accessed Dec. 12, 2019, 2 pages.
Corning® Preassembled Closed Systems Solution Centrifuge Tubes, Corning website catalog (https://ecatalog.corning.com/life-sciences/b2c/US/en/Liquid-Handling/Tubes), date unkn.

* cited by examiner

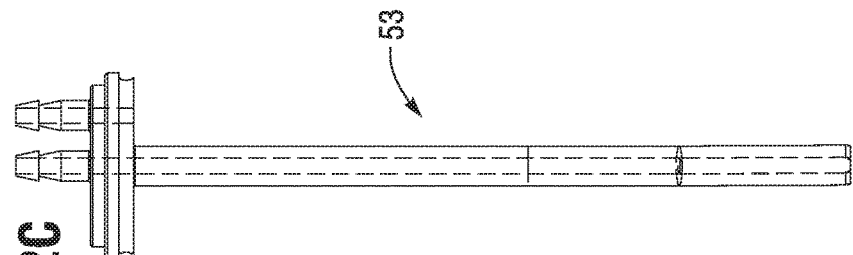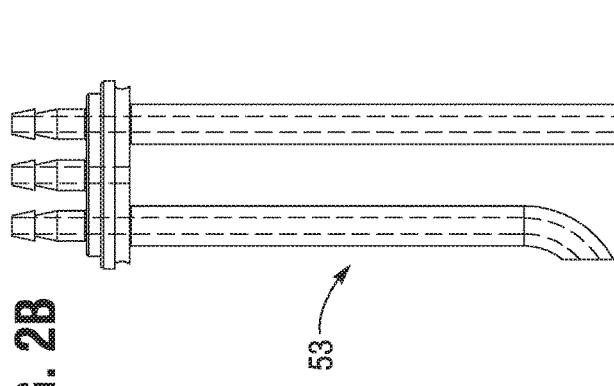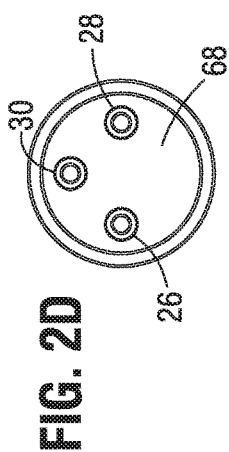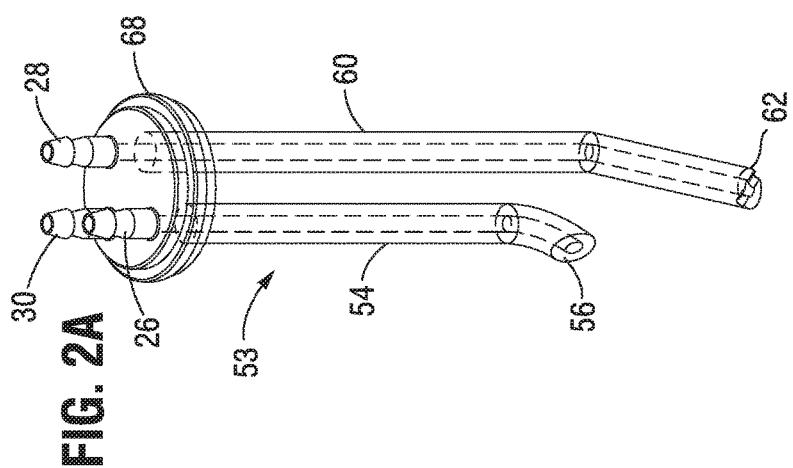

CLOSED FLUID RECEIVING AND SAMPLING CONTAINER

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

RELATED APPLICATION INFORMATION

This application is an original filing.

BACKGROUND

Field

This disclosure relates to a closed system for receiving liquid chemical or biological reaction products that facilitates sampling.

Description of the Related Art

Various chemical and biological reactions generate liquid reaction products that are often quite valuable due to a number of factors, including the fragile nature of the reaction and limited yield. Recovering the target product from the surrounding media can be difficult.

For instance, bioreactors that generate stem cells often require multiple stages and yield a relatively small amount of usable cells. To separate the cells from the surrounding media, various techniques are known, including bead separation. Bead separation relies on the capacity of small beads to bond to the substance of interest, which locates that substance on the beads for easier retrieval. For instance, the Invitrogen division of ThermoFisher Scientific based in Carlsbad, Calif. offers the Dynabeads magnetic separation technology for this purpose (https://www.thermofisher.com/us/en/home/brands/product-brand/dynal.html). The liquid product from a reaction is ported to a container such as a test tube which contains small beads. The beads are magnetically attractive and are coated so as to bind to the target material, e.g., stem cells, T-cells, nucleic acids, proteins, etc. The container is placed in a housing having a magnetic field along one side so that the beads collect in one area. The remaining media can then be drained away, leaving the valuable cells adhered to the beads. The cells may be used still attached to the beads, or the cells are washed from the beads with an inert solution and then recovered.

The process described above requires transport of the cell culture from the reactor to the microbead container, which can introduce contamination. There remains a need for a way to transfer valuable reaction liquid to a separation container without risking loss of sterility.

SUMMARY OF THE INVENTION

The present application discloses a sampling container that enables transfer of valuable reaction liquid to a separation container without risking loss of sterility. The sampling container is especially useful in the context of magnetic bead separation processes.

The sampling container has a dip tube subassembly with a shorter inlet tube bent towards the wall of the container to prevent or reduce foaming, and a longer outlet tube used to drain the waste liquid once the magnetic beads are trapped by the magnet. This allows for the introduction of product through the inlet tube and withdrawal of all of the waste liquid through the outlet tube which goes all the way to the bottom for the removal of every last drop. The dip tube subassembly has a sealed lid also with a vent tube therethrough which provides the ability to fill and drain the container without removing the lid, thus keeping the process aseptic. The sampling container disclosed herein essentially provides a closed system with built-in pipettes. The container has an injection molded dip tube subassembly providing a sealed barrier lid that incorporates the vent and pipette tubes.

DESCRIPTION OF THE DRAWINGS

FIG. 2A is a perspective view of an input/output insert for the fluid receiving and sampling container, and FIGS. 2B-2D are orthogonal views thereof.

DETAILED DESCRIPTION

The present application discloses a sealed container for receiving and sampling fluid without opening the container. The container may be provided in a variety of sizes, including small flasks or test tubes that are useful in magnetic bead separation technology. Although the sealed container is especially useful with bead separation technology, other applications are contemplated and the system should not be considered limited to any particular usage.

Figure 1A:
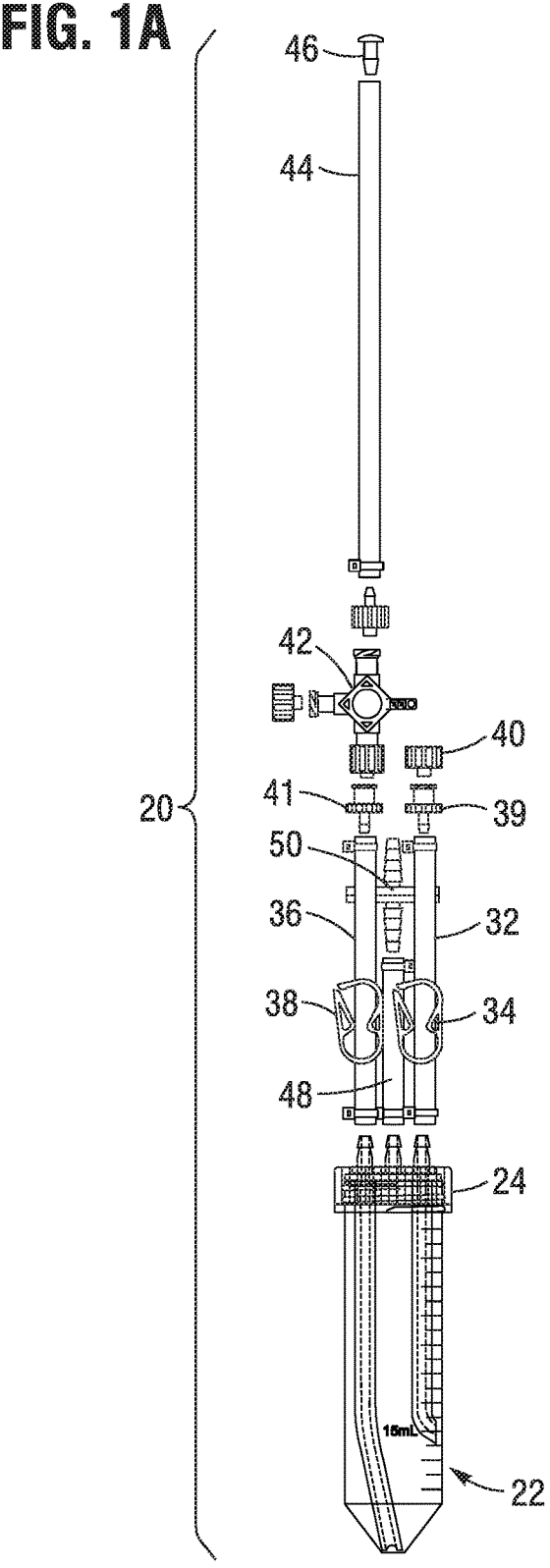
FIG. 1A is an elevational view of an exemplary fluid receiving and sampling container along with complementary fluid connections.
Figure 1B:
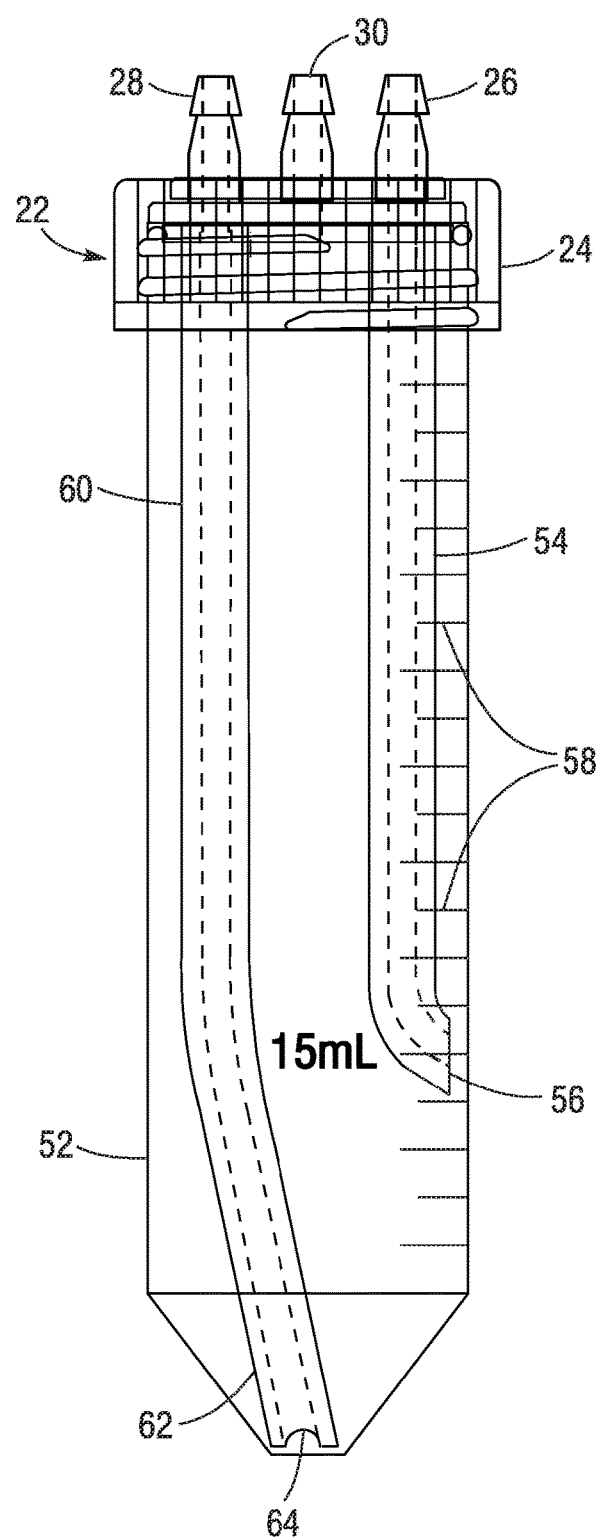
FIG. 1B shows the container enlarged.

FIG. 1A is an elevational view of an exemplary system 20 including a sealed fluid receiving and sampling container 22 along with complementary fluid connections, and FIG. 1B shows the container enlarged. The container 22 has a cap ring 24 that secures an injection molded subassembly 53 (see FIGS. 2A-2D) with at least three upstanding connectors. In particular, an inlet connector 26, an outlet connector 28, and a vent connector 30 are shown in FIG. 1B. The connectors 26, 28, 30 may be barbed fittings or other such configurations for mating with flexible tubes, or other known fluid connectors.

FIG. 1A shows an assembly of tubes and associated hardware to provide communication with the interior of the container 22. Namely, a first flexible tube 32 having an on/off pinch valve 34 may be connected to the inlet connector 26, and a second flexible tube 36 having an on/off pinch valve 38 connects to the outlet connector 28. An intermediate fitting 39 may be provided at an outer end of the first flexible tube 32 for mating with a source fitting (not shown), and a cap or plug 40 can be used to seal the intermediate fitting. A similar intermediate fitting 41 can be attached to the outer end of the second flexible tube 36 for mating with an outlet fitting, such as provided on a three-way stopcock 42. From there, the junctions on the stopcock 42 enable distribution of the fluid from the outlet tube 60 in several directions, such as through a third flexible tube 44 having a removable plug 46 on its distal end.

A vent tube 48 leads from the vent connector 30 to a disc filter 50. The atmosphere within the container 22 may require special filtering to avoid toxicity or other contamination of the laboratory environment.

The sealed fluid receiving and sampling container 22 is shown enlarged in FIG. 1B, and includes a closed bottom receptacle 52 having an open upper end to which the cap ring 24 attaches. The insert subassembly 53 shown in FIGS. 2A-2D is retained within an interior cavity of the receptacle 52 by the cap ring 24. For instance, the cap ring 24 has an outer tubular wall with internal threads that engage external threads on the open upper end of the receptacle 52, or the parts may be secured using a different coupling or adhesive/bonding.

The insert subassembly 53 comprises an inlet tube 54 leading downward from the inlet connector 26 to a curved lower end 56. The lower end 56 preferably curves 90° or less radially outward and terminates closely adjacent an inner wall of the receptacle 52 to reduce foaming of any fluid entering the container. More specifically, an end face of the lower end 56 is desirably angled perpendicular so as to face the adjacent inner wall of the receptacle 52. Thus, if the inner wall of the receptacle 52 is vertical, as shown, the lower end 56 curves 90°. However, for receptacles with curved or angled walls, the lower end 56 curves less than 90°, such as 63°, down to an angle as small as 20°.

Volumetric index marks 58 are desirably provided on the exterior of the receptacle 52.

In a preferred embodiment, the curved lower end 56 curves radially outward into close proximity with an inner wall of the receptacle 52 at a 15 mL index mark. In one embodiment, the curved lower end 56 is spaced as close as 0.1 inches or less from the inner wall of the receptacle 52.

The insert subassembly 53 also includes a siphon or outlet tube 60 leading downward from the outlet connector 28 to an angled siphon end 62 in close proximity to a lower end of the receptacle 52. The lower end of the receptacle 52 may be tapered so that the siphon end 62 is capable of removing all but trace amounts of liquid within the receptacle. As the outlet tube 60 is not centered in a disk-shaped lid 68, the siphon end 62 may be slightly angled relative to a longitudinal axis of the receptacle 52 to reach the tapered bottom end. Further, the lower siphon end 62 may have a small cut out 64 formed perpendicularly across its longitudinal axis which helps prevent the siphon end 62 from sealing against the lower end of the receptacle 52 due to suction. In one embodiment, the siphon end 62 reaches to within 0.05 inches of the bottom of the receptacle 52, and preferably about 0.03 inches.

The three connectors 26, 28, 30 and tubes 54, 60 are fixed with respect to the disk-shaped lid 68. The lid 68 fits closely within an upper end of the receptacle 52 and is sealed therein by the cap ring 24. The cap ring 24 has an annular radial flange that holds the lid 68 down, and an aperture large enough to accommodate passage of the connectors 26, 28, 30. The lid 68 may have an elastomeric outer periphery to provide a fluid seal against an inner surface of the receptacle 52. In this way, the only three avenues of fluid communication between the internal cavity of the receptacle 52 and the outside is through the three connectors 26, 28, 30. Fluid enters the receptacle 52 through the inlet connector 26 and inlet tube 54, and may be withdrawn through the outlet tube 60 and outlet connector 28. Any excess pressure created by the fluid transfer may result in air or other gas venting through the vent connector 30.

The insert subassembly 53 is desirably injection molded in one piece of a suitable polymer, such as polypropylene. The term "injection molded in one piece" means that the subassembly 53 is formed in a single manufacturing operation from a homogenous polymer so that there are no separable parts. This not only creates efficiencies of fabrication but reduces the potential for contamination during assembly with the receptacle 52 and cap ring 24 as well as during integration with a larger assembly and during use. In an exemplary embodiment, the receptacle 52 is also polypropylene has a capacity of 50 mL, but sizes as large as 500 ml are contemplated. The vertical height of the smaller 50 ml insert subassembly 53 may be around 5 inches, with the height of the receptacle 52 being slightly less. The inlet and outlet tubes 54, 60, as well as the vent connector 30 may have a variety of inner diameters, such as around 0.1 inches. Of course, these dimensions are exemplary and can be modified and scaled up for larger systems.

Figure 3:
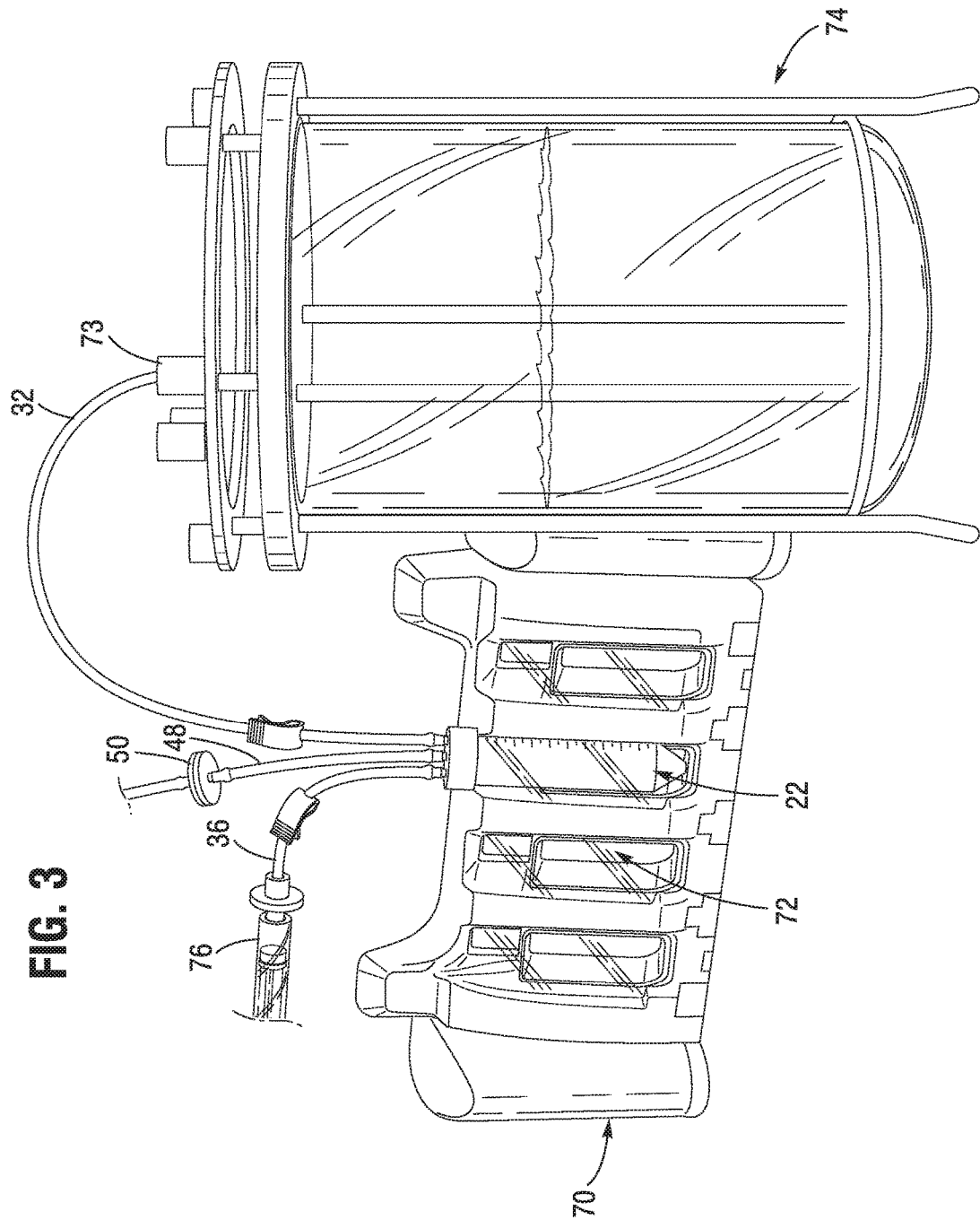
FIG. 3 shows an exemplary system incorporating the fluid receiving and sampling container which uses magnetic beads to separate usable cells from surrounding media.

FIG. 3 shows an exemplary system incorporating the fluid receiving and sampling container 22. In this context, the container 22 is held vertically by a stand 70 having a plurality of stations 72 adapted for holding the container. The first flexible tube 32 that attaches to the inlet connector 26 extends to an outlet 73 of a source of fluid such as a bioreactor 74. The source of fluid may be a chemical or biological reactor, a larger fluid receptacle, or a flask similar to the container 22 described herein. The second flexible tube 36 in communication with the outlet connector 28 extends to a receiving container such as a syringe 76.

The entire system 20 such as shown in FIG. 1A may be sold as a closed, sterile assembly in suitable sterile packaging. A user need only remove the various plugs and attached the inlet and outlet connectors to appropriate source and receiving containers to effectuate retrieval and sampling of the desirable liquid. The system 20 remains closed during the entire process, which greatly reduces the chance of any contamination, thus increasing aggregate yield of the final product.

A useful application for the seal receiving and sampling container 22 uses magnetic beads to separate usable cells from surrounding media. More particularly, small magnetic beads are coated with a material which attracts desirable cells. The stand 70 has magnets or is magnetized on its inner vertical wall at each of the stations 72 which attracts the magnetic beads suspended in fluid within the container 22 and holds them against the inside wall of the container. With the magnetic beads immobilized in this manner, any residual chemical media may be withdrawn through the outlet tube 60 using the syringe 76, for example, and discarded or otherwise utilized if desired. Subsequently, additional washing fluid may be introduced to the container 22 to separate the desirable cells from the magnetic beads. By placing the container 22 once more in the stand 70, the cleaned magnetic beads maybe once again immobilized so that the cells within the wash fluid can be removed through the outlet tube 60 and exterior tube 36.

Figure 4:
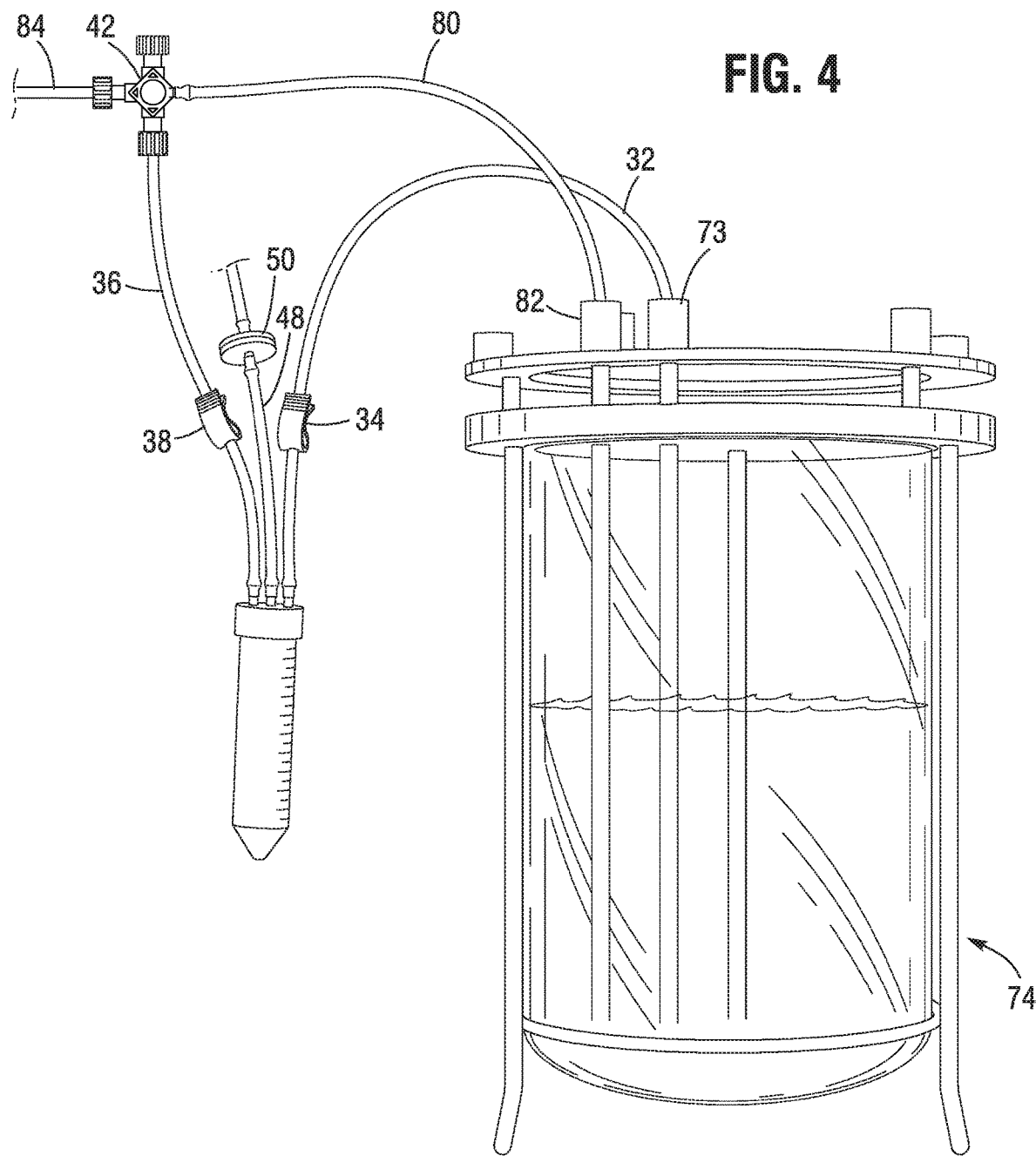
FIG. 4 shows another exemplary system incorporating the fluid receiving and sampling container to recirculate medium from a bioreactor.

FIG. 4 shows another exemplary system incorporating the fluid receiving and sampling container 22 to recirculate medium from a bioreactor 74. Some cell therapy applications utilize medium recirculation to enhance the equality of cells in growth phase, expansion and differentiation. Medium may be ported through the bioreactor outlet 73 to the container 22, and then through the flexible tube 36 and back via the stopcock 42 and return passage or tube 80 into a bioreactor inlet 82. Recirculation of medium through container 22 has the ability to remove waste while allowing the cells to either remain in the bioreactor and/or pass through the enclosed loop without exposing cells to risk of contamination. In addition, the stopcock 42 may be used to alter the flow path of the recirculating medium to a sampling or diverter tube 84 to be redirected into a subsequent processing container (not shown). Again, the sealed nature of the system 20 including the fluid receiving and sampling container 22 provides a "plug-and-play" assembly which may be readily connected to the bioreactor 74 to supply a recirculation loop without risk of contamination.

Terms such as top, bottom, left and right are used herein, though the fluid manifolds may be used in various positions such as upside down. Thus, some descriptive terms are used in relative terms and not absolute terms.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

As used herein, "plurality" means two or more. As used herein, a "set" of items may include one or more of such items. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It is claimed:

1. A chemical or biological processing assembly including:
   a closed system for receiving and sampling liquid, comprising:
   i. a receptacle having a closed lower end and an open top end;
   ii. a subassembly of a lid capable of sealing over the open top end of the receptacle, an inlet tube extending downward from the lid in communication with an inlet connector projecting upward from the lid, and outlet tube extending downward from the lid in communication with an outlet connector projecting upward from the lid, and a vent connector projecting upward from the lid and having an opening to a lower side of the lid, wherein the subassembly is configured to seal over the top end of the receptacle with the inlet tube and the outlet tube extending downward into an inner volume of the receptacle, and wherein the outlet tube extends farther downward than the inlet tube; and
   iii. a cap ring configured to be secured around the open top end of the receptacle so as to retain the lid over the open top end; and
   a reactor containing a liquid reaction medium with a reactor outlet and reactor outlet tube attached to the inlet connector of the subassembly, a stand having a plurality of stations adapted for holding the receptacle, the stand having magnets or is magnetized on an inner vertical wall at each of the stations, and wherein the receptacle contains magnetically-attractive beads configured to attract a desirable component of the liquid reaction medium, such that the desirable component may be isolated on the beads and held against an inner wall of the receptacle adjacent the inner vertical wall of a respective station.

2. The assembly of claim 1, wherein the inlet tube extends vertically downward and curves radially outward at a lower end, and is configured to be spaced closely adjacent to an inner wall of the receptacle at the lower end.

3. The assembly of claim 2, wherein the lower end curves 90° or less and an end face of the lower end is angled perpendicular so as to face the inner wall of the receptacle at the lower end.

4. The assembly of claim 1, wherein the outlet tube reaches to within 0.05 inches of a bottom end of the receptacle.

5. The assembly of claim 1, wherein the outlet tube has a small cut out across its longitudinal axis at its lower end to prevent the lower end from sealing against the bottom end of the receptacle from suction.

6. The assembly of claim 1, wherein the receptacle tapers inward at a bottom end, and a lower siphon end of the outlet tube angles so as to reach a central location of the bottom end.

7. The assembly of claim 1, wherein the subassembly is injection molded as one piece.

8. The assembly of claim 7, wherein the subassembly is made of polypropylene.

9. The assembly of claim 1, further including a flexible first tube connected to the inlet connector and a first plug for sealing the flexible first tube, and a flexible second tube connected to the outlet connector and a second plug for sealing the flexible second tube.

10. The assembly of claim 9, further including a three-way stopcock adapted to be coupled to the flexible second tube to enable distribution of the fluid from the outlet tube in multiple directions.

11. The assembly of claim 1, further including a vent filter connected to the vent connector.

12. The assembly of claim 1, further including a plug on both the inlet tube and the outlet tube to seal the tubes prior to use.

13. The assembly of claim 1, further including a flexible first tube connected to the inlet connector, and a flexible second tube connected to the outlet connector, and an on/off pinch valve on both the flexible first tube and the flexible second tube to enable manual opening and closure of flow therethrough.

14. The assembly of claim 1, wherein there are a plurality of the closed systems placed in the plurality of stations of the stand each of which is connected to receive liquid reaction medium from the reactor.

15. The assembly of claim 1, further including a syringe attached to the outlet connector of the closed system for sampling fluid from within the receptacle.

16. A chemical or biological processing assembly including:
   a closed system for receiving and sampling liquid, comprising:
   i. a receptacle having a closed lower end and an open top end;
   ii. a subassembly of a lid capable of sealing over the open top end of the receptacle, an inlet tube extending downward from the lid in communication with an inlet connector projecting upward from the lid, and outlet tube extending downward from the lid in communication with an outlet connector projecting upward from the lid, and a vent connector projecting upward from the lid and having an opening to a lower side of the lid, wherein the subassembly is configured to seal over the top end of the receptacle with the inlet tube and the outlet tube extending downward into an inner volume of the receptacle, and wherein the outlet tube extends farther downward than the inlet tube; and iii. a cap ring configured to be secured around the open top end of the receptacle so as to retain the lid over the open top end; and a reactor containing a liquid reaction medium with a reactor outlet and reactor outlet tube attached to the inlet connector of the subassembly, and a three-way stopcock attached to the outlet connector of the closed system, a return tube connected to a junction of the three-way stopcock and also to a return inlet to the reactor, and a sampling tube connected to a junction of the three-way stopcock.

17. The assembly of claim 16, wherein the inlet tube extends vertically downward and curves radially outward at a lower end, and is configured to be spaced closely adjacent to an inner wall of the receptacle at the lower end.

18. The assembly of claim 17, wherein the lower end curves 90° or less and an end face of the lower end is angled perpendicular so as to face the inner wall of the receptacle at the lower end.

19. The assembly of claim 16, wherein the outlet tube reaches to within 0.05 inches of a bottom end of the receptacle.

20. The assembly of claim 16, wherein the outlet tube has a small cut out across its longitudinal axis at its lower end to prevent the lower end from sealing against the bottom end of the receptacle from suction.

21. The assembly of claim 16, wherein the receptacle tapers inward at a bottom end, and a lower siphon end of the outlet tube angles so as to reach a central location of the bottom end.

22. The assembly of claim 16, wherein the subassembly is injection molded as one piece.

23. The assembly of claim 22, wherein the subassembly is made of polypropylene.

24. The assembly of claim 16, further including a flexible first tube connected to the inlet connector and a first plug for sealing the flexible first tube, and a flexible second tube connected to the outlet connector and a second plug for sealing the flexible second tube.

25. The assembly of claim 16, further including a vent filter connected to the vent connector.

26. The assembly of claim 16, further including a plug on both the inlet tube and the outlet tube to seal the tubes prior to use.

27. The assembly of claim 16, further including a flexible first tube connected to the inlet connector, and a flexible second tube connected to the outlet connector, and an on/off pinch valve on both the flexible first tube and the flexible second tube to enable manual opening and closure of flow therethrough.

* * * * *